US005766577A

United States Patent [19]
Hechavarria

[11] Patent Number: 5,766,577
[45] Date of Patent: Jun. 16, 1998

[54] COLOR COSMETIC COMPOSITION

[75] Inventor: Caridad Hechavarria, New Haven, Conn.

[73] Assignee: Elizabeth Arden Co., Division of Conopco, Inc., New York, N.Y.

[21] Appl. No.: 943,076

[22] Filed: Sep. 10, 1992

[51] Int. Cl.$^6$ .............. A61K 7/021; A61K 7/00; A61K 7/42
[52] U.S. Cl. .............. 424/63; 424/60; 424/69; 424/400; 424/401; 514/772; 514/844
[58] Field of Search .............. 424/60, 69, 63, 424/400, 401; 514/772, 844

[56] References Cited

U.S. PATENT DOCUMENTS

| | | | |
|---|---|---|---|
| 3,923,971 | 12/1975 | Seilinger | 424/63 |
| 4,272,514 | 6/1981 | Spence | 424/69 |
| 4,379,136 | 4/1983 | Mochida | 424/47 |
| 4,882,225 | 11/1989 | Fukui et al. | 428/405 |
| 5,015,263 | 5/1991 | Albrecht et al. | 424/63 |
| 5,206,012 | 4/1993 | Farer et al. | 424/69 |

FOREIGN PATENT DOCUMENTS

| | | | |
|---|---|---|---|
| 0136213 | 10/1980 | Japan | 424/63 |
| 62-49247 | 10/1987 | Japan | 428/405 |

*Primary Examiner*—Shelley A. Dodson
*Attorney, Agent, or Firm*—Milton L. Honig

[57] ABSTRACT

A powdered molded color cosmetic composition is provided that includes a talc having average particle size between 2 and 8 microns and a mica with an average particle size between 2 and 8 microns.

4 Claims, No Drawings

COLOR COSMETIC COMPOSITION

BACKGROUND OF THE INVENTION

1. Field of the Invention

The invention relates to a color cosmetic composition in powder form.

2. The Related Art

Molded powder color cosmetics in major part consist of fillers and extenders. Most often they are of the mineral variety. Illustrative are talc, kaolin, mica and silicon dioxide. In more limited amount, the extenders or fillers may be organic polymers including nylon and polyethylene. Often one or more of the aforementioned substances are blended together. These blends utilize relative proportions determined from consideration of skinfeel, spreadability, opacifying effect, moldability and adherence.

Typical of this technology are the disclosures found in U.S. Pat. No. 4,882,225 (Fukui et al) and Japanese Patent 62-49427 (Ohno et al). Despite advances in the art, there remains considerable room for improvement in the aesthetic and performance properties of molded powder color cosmetics.

Accordingly it is an object of the present invention to provide a pressed powder color cosmetic composition which exhibits improved properties of skinfeel, spreadability, creaminess, adhesion to skin and smoothness.

A further object of the present invention is to provide a pressed powder cosmetic color composition with good compression in manufacture.

A still further object of the present invention is to provide a pressed powder cosmetic color composition that is neither too dusty nor brittle.

These and other objects of the present invention will become more apparent by consideration of the following summary, detailed description and examples.

SUMMARY OF THE INVENTION

A powder color cosmetic composition is provided that includes:

(i) a talc of average particle size ranging from 2 to 8 microns present in an effective amount to provide hardness to the cosmetic; and (ii) a mica of an average particle size ranging from 2 to 8 microns present in an effective amount to modify firmness of the cosmetic.

DETAILED DESCRIPTION

Now it has been found that an improved pressed powder color cosmetic can be achieved that combines a talc and a mica, each of a particle size ranging from about 2 to 8 microns. Good compressibility (hardness) and cushion (softening of the cake) is achieved with the combination. According to the present invention, the talc may have a hydrophobic or hydrophilic surface, the former being achieved through treatment with a silicone such as a methicone.

Amounts of the talc may range anywhere from about 1 to about 95%, preferably between about 30 and 70%, optimally between about 40 and 60% by weight. Talc average particle size should range from 2 to 8 microns, optimally between about 6 and 8 microns.

The second component of this invention is a mica which may be selected from muscovite, phlogopite, tiotite, sericite, lepidolite, paragonite and artificial or synthetic mica having a fluorine atom substituted for the hydroxyl group of natural mica as well as baked or calcined products thereof. These mica may be used alone or in any mixture thereof. Particularly preferred is a hydrophobic mica wherein the mineral has been coated with a silicone compound such as cyclomethicone or dimethicone. Amounts of the mica may range anywhere from about 1 to about 95%, preferably between about 30 and 70%, optimally between about 40 and 60% by weight. Mica average particle size should range from 2 to 8 microns, optimally between about 6 and 8 microns.

In addition to the critical two components, there also may be present inorganic pigments, metal oxide and hydroxides, pearling pigments, organic pigments, mineral silicates, porous materials, carbons, metals, biopolymers and combinations thereof.

Examples of inorganic pigments are ultramarine blue, Prussian blue, manganese violet and bismuth oxychloride.

Examples of metal oxides and hydroxides useful in the present invention are magnesium oxide, magnesium hydroxide, magnesium carbonate, calcium oxide, calcium hydroxides, aluminum oxide, aluminum hydroxide, silica, iron oxides ($\alpha$-$Fe_2O_3$, $\gamma$-$Fe_2O_3$, $Fe_3O_4$, FeO), iron hydroxides, titanium dioxide, titanium lower oxides, zirconium oxides, chromium oxides, chromium hydroxides, manganese oxides, cobalt oxides, nickel oxides and zinc oxides. These oxides and hydroxides may be used alone or in any mixture thereof. Furthermore, composite oxides and composite hydroxides such as iron titanate, cobalt titanate and cobalt aluminate can also be used in the present invention. Composite materials comprising metal oxides or hydroxides coated on the core materials (e.g. titanium oxides and iron oxides coated nylon) also can be used in the present invention.

Examples of organic pigments suitable for the present invention are C.I. 15850, C.I. 15850:1, C.I. 15585:1, C.I. 15630, C.I. 15880:1, C.I. 73360, C.I. 12085, C.I. 15865:2, C.I. 12075, C.I. 21110, C.I. 21095, and C.I. 11680, C.I. 74160 and zirconium, barium or aluminum lakes of C.I. 45430, C.I. 45410, C.I. 45100, C.I. 17200, C.I. 45380, C.I. 45190, C.I. 14700, C.I. 15510, C.I. 19140, C.I. 15985, C.I. 45350, C.I. 47005, C.I. 42053 and C.I. 42090.

The surfaces of these organic pigments may be treated with, for example, resins. These organic pigments may be used alone or in any mixture thereof.

Examples of pearling pigments (or nacreaous pigments) are bismuth oxychloride, guanine and titanium composite materials containing, as a titanium component, titanium dioxide, titanium lower oxides or titanium oxynitride. The titanium composite materials may be mixed with colored pigments such as iron oxides, Prussian blue, chromium oxide, carbon black and carmine. These pearling pigments may be used alone or in any mixture thereof.

Examples of mineral silicates suitable for the present invention are phyllosilicates and tectosilicates such as pyrophyllite, chlorite, chrysotile, antigorite, lizardite, kaolinite, dickite, nacrite, halloysite, montmorillonite, nontronite, saponite, sauconite, and bentonite; natrolites such as natrolite, mesolite, scolecite, and thomsonite; heulandites such as heulandite, stilbite, epistibite; and zeolites such as analcite, harmotone, phillipsite, chabazite and gmelinite. These silicate minerals may be used alone or in combination thereof. The phyllosilicates may have organic cations at the interface of the layers thereof or may be substituted with alkali metal or alkaline earth metal ions. The tectosilicates may include metallic ions in the fine pores thereof.

Examples of porous materials suitable for the present invention are the above-mentioned silicate minerals; the above-mentioned metal oxides; $KAl_2(Al\ Si_3)O_{10}F_2$, $KMg(Al,\ Si_3)O_{10}F_2$, and $K(Mg,Fe_3)(Al,\ Si_3)O_{10}F_2$; carbonate minerals such as $CaCO_3$, $MgCO_3$, $FeCO_3$, $MnCO_3$, $ZnCO_3$, $CaMg(CO_3)_2$, $Cu(OH)_2CO_3$, and $Cu_3(OH)_2(CO_3)_2$; sulfate minerals such as $BaSO_4$, $PbSO_4$, $CaSO_4$, $CaSO_4 \cdot 2H_2O$, $CaSO_4 \cdot 5(H_2O)$, $Cu_4SO_4(OH)_6$, $KAl_3(OH)_6(SO_4)_2$, and $KFe_3(OH)_6(SO_4)$; phosphate minerals such as $YPO_4$, $(CeLa)PO_4$, $Fe_3(PO_4)_2 \cdot 8H_2O$, $Ca_5(PO_4)_3OH$ and $Ca_5(PO_4CO_3OH)_3F$, $OH$); and metal nitrides such as titanium nitride and chromium nitride. These materials may be used alone or in any mixture thereof.

Examples of metals suitable for the present invention are iron, cobalt, nickel, copper, zinc, aluminum, chromium, titanium, zirconium, molybdenum, silver, indium, tin, antimony, tungsten, platinum and gold, and the alloys thereof.

Powdery biopolymer materials are also suitable for the present invention, especially by virtue of their high safety factor.

Examples of biopolymer materials suitable for the present invention are keratin (hair, fur, feather, down, horn, hoof, etc.), fibroin (silk), collagen (skin, hide, leather, tendon, bond, etc.), cellulose, hemicellulose, pectin, chitin, chondroitin, peptide-glucan, nucleic acid (DNA, RNA) and the like.

A variety of boron nitrides may also be employed. Average particle size for such material may range from about 0.1 to about 30 microns, preferably between about 3 and 7 microns. Amounts of the boron nitride may range from about 0.001 to about 30%, optimally between about 1 to 10% by weight.

Any conventional cosmetic ingredients can be used together with the powder materials. Typical examples of such ingredients are various hydrocarbons such as squalane, liquid paraffin, and microcrystalline wax; emollient acids and alcohols such as caprylic acid, myristic acid, palmitic acid, stearic acid, oleic acid, isostearic acid, cetyl alcohol, hexadecyl alcohol and oleyl alcohol; emollient esters such as caprylate esters, cetyl-2-ethylhexanoate, ethylhexyl palmitate, 2-octyldodecyl myristate, 2-octyldodecyl gum ester, neopentyl glycol-2-ethylhexanoate, isooctyl triglyceride, 2-octyldodecyl oleate, isopropyl myristate, isostearic acid triglycerides, coconut oil fatty acid triglyceride, olive oil, avocado oil, beeswax, myristyl myristate, mink oil, lanolin and dimethyl polysiloxane; resins such as alkyd resins and urea resins; plasticizers such as camphor and acetyl tributyl citrate; UV absorbers; antioxidants; preservatives; surfactants; humectants; perfumes; water; alcohols and thickening agents.

Among the preservatives useful for the present invention are phenoxyethanol, ethyl paraben, isobutyl paraben, n-butyl paraben, methyl paraben, propyl paraben, sodium dehydroacetate and combinations thereof. The amount of preservative may range from about 0.01 to about 5%, preferably between about 0.10 and 2%, optimally between about 0.4 and 1% by weight.

Various herbal extracts may also be employed. Examples of these extracts are rosemary, althea, sambucus, matricaria and combinations thereof. Levels of the extract may range from 0.0001 to about 10%, preferably about 0.1 to about 2% by weight.

Compositions of the present invention advantageously will have all components of a similar average particle size, preferably between about 1 and about 8 microns, optimally between 2 and 7 microns. Uniformity of particle size may either be achieved by separately combining components of the proper size or by shear mixing the total composition down to the desired particle size range. A jet mill is particularly useful for purposes of shearing the total composition.

The following Examples will more fully illustrate the embodiments of the present invention. All parts, percentages and proportions referred to herein and in the appended claims are by weight unless otherwise indicated.

EXAMPLE 1

An eye shadow formula according to the present invention which has been jet milled is outlined under Table I.

TABLE I

| Chemical or CTFA Name | Weight % |
|---|---|
| Hydrophobic Talc | 40 |
| Hydrophobic Mica | 40 |
| Silica Beads | 3.8–5 |
| Zinc Stearate | 0–6 |
| Nylon 12 | 2–4 |
| Boron Nitride | 5.00 |
| Methyl Paraben | 0.20 |
| Propyl Paraben | 0.10 |
| Sodium Dehydroacetate | 0.20 |
| Bismuth Oxychloride | 0–10 |
| Matricaria Extract | 0–1 |
| Rosemary Extract | 0–1 |
| Althea Extract | 0–1 |
| Sambucus Extract | 0–1 |
| Octyl palmitate | 0–5 |
| Pentaerythritol tetra(2-ethyl hexanoate) | 0–5 |
| Dimethicone | 0–5 |
| Colorants | 1–30 |

Colorants listed below will vary in percentages due to shade. The colorant can range from 1 to 30% depending upon the shade.
Carmine C.I. 75470
Chromium Oxide, Hydrous Green C.I. 77289
Chromium Oxide, Anhydrous Green C.I. 77288
Ultramarine Rose C.I. 77007
Brown Iron Oxide C.I. 77491, 2, 9
Red Iron Oxide C.I. 77491
Russet Iron Oxide C.I. 77491
Yellow Iron Oxide C.I. 77492
Black Iron Oxide C.I. 77499
Manganese Violet C.I. 77742
Ultramarine Blue C.I. 7707
Titanium Dioxide C.I. 77891
Prussian Blue C.I. 77510
Pearl Substrate: Mica and/or $TiO_2$; Carmine; Iron Oxides; Ferric Ferrocyanide; Ultramarine Rose; Manganese Violet; Chromium Oxide Hydrous/Anhydrous Green; Ferrocyanide; Bismuth Oxychloride.

EXAMPLE 2

A blush formula according to the present invention which has been jet milled is outlined under Table II.

TABLE II

| Chemical or CTFA Name | Weight % |
|---|---|
| Talc BC | 36 |
| Mica | 36 |

TABLE II-continued

| Chemical or CTFA Name | Weight % |
|---|---|
| Mica & Silicon Dioxide | 4.00 |
| Bismuth Oxychloride | 2.00 |
| Magnesium Myristate | 2.00 |
| Boron nitride | 5.00 |
| Methyl paraben | 0.20 |
| Propyl paraben | 0.10 |
| Sodium Dehydroacetate | 0.20 |
| Dimethicone | 1.25–2.25 |
| Pentaerythritol tetra(2-ethyl hexanoate) | 1.25–2.25 |
| Octyl palmitate | 1.25–2.25 |
| Colorants | 8–10 |

Colorants listed below will vary in percentages due to shade. The colorant can range from 1 to 10% depending upon the shade. Total pigment level of blusher is approximately 8 to 10%.

D&C Red 7 C.I. 15850:1
D&C Yellow 5 C.I. 19140:1
D&C Red 30 C.I. 73360
D&C Red 6 C.I. 15850
D&C Orange 4 C.I. 15510
Carmine C.I. 75470
Chromium Oxide, Hydrous Green C.I. 77289
Chromium Oxide, Anhydrous Green C.I. 77288
Ultramarine Rose C.I. 77007
Brown Iron Oxide C.I. 77491, 2, 9
Red Iron Oxide C.I. 77491
Russet Iron Oxide C.I. 77491
Yellow Iron Oxide C.I. 77492
Black Iron Oxide C.I. 77499
Manganese Violet C.I. 77742
Ultramarine Blue C.I. 7707
Titanium Dioxide C.I. 77891
Prussian Blue C.I. 77510
Pearl Substrate: Mica and/or $TiO_2$; Carmine; Iron Oxides; Ferric Ferrocyanide; Ultramarine Rose; Manganese Violet; Chromium Oxide Hydrous/Anhydrous Green; Ferrocyanide; Bismuth Oxychloride.

EXAMPLE 3

A set of experiments were conducted to demonstrate criticality of particle size with respect to the talc and mica. Table III lists the formulation components. The binder is an approximately equal weight mixture of octyl palmitate, pentaerythritol tetra(2-ethyl hexanoate) and dimethicone.

TABLE III

| Component | A | B | C | D | E | F |
|---|---|---|---|---|---|---|
| Talc (2–8 micron) | 47.5 | 95.0 | — | — | 47.5 | — |
| Talc (10–15 micron) | — | — | — | 47.5 | — | 47.5 |
| Mica (2–8 micron) | 47.5 | — | 95.0 | — | — | 47.5 |
| Mica (15–30 micron) | — | — | — | 47.5 | 47.5 | — |
| Binder | 3.0 | 3.0 | 3.0 | 3.0 | 3.0 | 3.0 |
| Red Iron Oxide (50%) | 2.0 | 2.0 | 2.0 | 2.0 | 2.0 | 2.0 |

Samples A–F were filled into respective pans. These were compressed at 800 psi down to a set fill line. Each pan had thus a uniform volume and ranged in weight from 2.4 to 3.4 grams. The resultant cakes were measured by a penetrometer. Three penetrometer determinations were conducted on each sample and the values averaged. Ordinarily, the penetrometer values will be acceptable when ranging from 7 to 15. Values less than 7 indicate an unacceptable brick-like cake. Values greater than 15 indicate cakes that are too soft and provide too much payoff when rubbed with a brush.

The Drop Test was utilized as measure of the firmness of each sample. Pass or fail indications were given for each.

TABLE IV

| Performance Properties | A | B | C | D | E | F |
|---|---|---|---|---|---|---|
| Penetrometer (mm) | 11.2 | 4.2 | 17.7 | 27.5 | 17.8 | 14.3 |
| Drop Test | Passed | Passed | Failed | Failed | Failed | Failed |

Samples C, D and E had penetrometer values outside the acceptable range. Each of these also failed the Drop Test. Although Sample F was just within the acceptable penetrometer values, this Sample also failed the Drop Test. Sample B had an unacceptable penetrometer value of 4.2. Only Sample A of the series tested had both an acceptable penetrometer value and passed the Drop Test. These results indicate that a combination of ultrafine talc and ultrafine mica provide a much better cosmetic cake than either material alone or any combination not having an ultrafine particle size.

The foregoing description and examples illustrate selected embodiments of the present invention. In light thereof, various modifications will be suggested to one skilled in the art, all of which are within the spirit and purview of this invention.

What is claimed is:

1. A powdered color cosmetic composition comprising:
   (i) a talc of average particle size ranging from 2 to 8 microns present in an amount from about 30 to 70% by weight to provide hardness to the cosmetic composition; and
   (ii) a mica of an average particle size ranging from 2 to 8 microns present in an amount from about 30 to 70% by weight to modify firmness of the cosmetic composition.

2. A composition according to claim 1 wherein the talc is present in an amount from about 40 to 60% by weight.

3. A composition according to claim 1 wherein the mica is present in an amount from about 40 to 60% by weight.

4. A powdered color cosmetic composition comprising:
   (i) a talc of average particle size ranging from 6 to 8 microns present in an amount from about 30 to 70% by weight to provide hardness to the cosmetic composition; and
   (ii) a mica of an average particle size ranging from 6 to 8 microns present in an amount from about 30 to 70% by weight to modify firmness of the cosmetic composition.

* * * * *